US010198780B2

(12) United States Patent
Walker et al.

(10) Patent No.: US 10,198,780 B2
(45) Date of Patent: *Feb. 5, 2019

(54) VIRTUAL HOME SAFETY ASSESSMENT FRAMEWORK (71) Applicant: CERNER INNOVATION, INC., Kansas City, KS (US)

(72) Inventors: James M. Walker, New Cumberland, PA (US); Jan DeHaan, Hawley, PA (US)

(73) Assignee: Cerner Innovation, Inc., Kansas City, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 15/661,989

(22) Filed: Jul. 27, 2017

(65) Prior Publication Data
US 2017/0323411 A1 Nov. 9, 2017

Related U.S. Application Data (63) Continuation of application No. 14/564,135, filed on Dec. 9, 2014, now Pat. No. 9,747,654.

(51) Int. Cl.
G06N 5/04 (2006.01)
G06Q 50/26 (2012.01)
G06F 19/00 (2018.01)
G06Q 10/10 (2012.01)
G16H 50/20 (2018.01)

(52) U.S. Cl.
CPC .......... *G06Q 50/265* (2013.01); *G06F 19/00* (2013.01); *G06F 19/3418* (2013.01); *G06N 5/04* (2013.01); *G06Q 10/10* (2013.01); *G16H 50/20* (2018.01)

(58) Field of Classification Search
CPC ................................ G06N 5/04; G06Q 50/265
USPC ........................................................ 348/143
See application file for complete search history.

(56) References Cited

U.S. PATENT DOCUMENTS

| 3,171,112 A | 2/1965 | Martin et al. |
| 5,601,435 A | 2/1997 | Quy et al. |
| 5,799,282 A | 8/1998 | Rakshit et al. |
| 5,913,310 A | 6/1999 | Brown et al. |

(Continued)

FOREIGN PATENT DOCUMENTS

| EP | 922434 A1 | 6/1999 |
| EP | 1110500 A2 | 6/2001 |

(Continued)

OTHER PUBLICATIONS

Moraru et al, Integrating wireless sensors into cloud systems for ambient assisted living (Year: 2017).*

(Continued)

*Primary Examiner* — Shan E Elahi
(74) *Attorney, Agent, or Firm* — Shook, Hardy & Bacon L.L.P.

(57) ABSTRACT

Disclosed herein is a framework for facilitating virtual safety assessment. In accordance with one aspect, the framework receives image data of an environment to be assessed for safety from an agent support system. The framework sends such image data to an expert support system and receives safety assessment information from the expert support system determined based on the image data. The framework then provides a report based at least in part on such safety assessment information.

18 Claims, 2 Drawing Sheets

(56) References Cited

U.S. PATENT DOCUMENTS

| | | | |
|---|---|---|---|
| 6,024,699 A | 2/2000 | Surwit et al. | |
| 6,280,198 B1 | 8/2001 | Calhoun et al. | |
| 6,334,778 B1 | 1/2002 | Brown | |
| 6,454,705 B1 | 9/2002 | Cosentino et al. | |
| 6,494,830 B1 | 12/2002 | Wessel | |
| 6,514,079 B1 | 2/2003 | McMenimen et al. | |
| 6,767,211 B2 | 7/2004 | Hall et al. | |
| 7,225,013 B2 | 5/2007 | Geva et al. | |
| 7,285,090 B2 | 10/2007 | Stivoric et al. | |
| 9,129,506 B1 | 9/2015 | Kusens | |
| 9,159,215 B1 | 10/2015 | Kusens | |
| 9,501,624 B2* | 11/2016 | Vishnubhatla | G06F 19/328 |
| 9,729,833 B1* | 8/2017 | Kusens | G06T 7/285 |
| 9,741,227 B1* | 8/2017 | Kusens | G08B 21/043 |
| 2002/0128746 A1* | 9/2002 | Boies | G06N 3/008 |
| | | | 700/245 |
| 2003/0058341 A1* | 3/2003 | Brodsky | G06K 9/00335 |
| | | | 348/169 |
| 2003/0120458 A1 | 6/2003 | Rao et al. | |
| 2003/0125984 A1 | 7/2003 | Rao et al. | |
| 2003/0125985 A1 | 7/2003 | Rao et al. | |
| 2003/0126101 A1 | 7/2003 | Rao et al. | |
| 2003/0130871 A1 | 7/2003 | Rao et al. | |
| 2003/0130973 A1 | 7/2003 | Sumner, II et al. | |
| 2003/0219709 A1 | 11/2003 | Olenick et al. | |
| 2004/0152957 A1 | 8/2004 | Stivoric et al. | |
| 2004/0172297 A1 | 9/2004 | Rao et al. | |
| 2004/0230105 A1 | 11/2004 | Geva et al. | |
| 2004/0243447 A1* | 12/2004 | Kamiyama | G06F 19/328 |
| | | | 705/3 |
| 2005/0043894 A1 | 2/2005 | Fernandez | |
| 2005/0090978 A1 | 4/2005 | Bathory et al. | |
| 2005/0131663 A1* | 6/2005 | Bangs | G16H 50/50 |
| | | | 703/11 |
| 2006/0154642 A1* | 7/2006 | Scannell, Jr. | A01G 9/02 |
| | | | 455/404.1 |
| 2006/0265253 A1 | 11/2006 | Rao et al. | |
| 2007/0100666 A1 | 5/2007 | Stivoric et al. | |
| 2007/0118399 A1 | 5/2007 | Avinash et al. | |
| 2007/0157385 A1 | 7/2007 | Lemire et al. | |
| 2007/0208232 A1 | 9/2007 | Kovacs | |
| 2008/0004904 A1 | 1/2008 | Tran | |
| 2008/0059242 A1 | 3/2008 | Stanford | |
| 2008/0162352 A1 | 7/2008 | Gizewski | |
| 2008/0171919 A1 | 7/2008 | Stivoric et al. | |
| 2008/0275309 A1 | 11/2008 | Stivoric et al. | |
| 2009/0005016 A1* | 1/2009 | Eng | A61B 5/411 |
| | | | 455/414.1 |
| 2009/0043216 A1 | 2/2009 | Lin et al. | |
| 2009/0099480 A1 | 4/2009 | Salgo et al. | |
| 2009/0119843 A1* | 5/2009 | Rodgers | A61B 5/1115 |
| | | | 5/611 |
| 2009/0124870 A1 | 5/2009 | Arends et al. | |
| 2009/0172773 A1 | 7/2009 | Moore | |
| 2009/0248450 A1 | 10/2009 | Fernandez | |
| 2010/0169111 A1 | 7/2010 | Brue et al. | |
| 2010/0217619 A1* | 8/2010 | Cox | G06F 19/3418 |
| | | | 705/2 |
| 2010/0228566 A1* | 9/2010 | Taylor | G06F 19/3462 |
| | | | 705/3 |
| 2010/0231421 A1 | 9/2010 | Rawls-Meehan | |
| 2011/0153356 A1 | 6/2011 | Kenedy et al. | |
| 2011/0263950 A1 | 10/2011 | Larson et al. | |
| 2011/0267189 A1* | 11/2011 | Stewart | G01S 13/92 |
| | | | 340/533 |
| 2012/0041782 A1 | 2/2012 | Morris | |
| 2012/0069131 A1 | 3/2012 | Abelow | |
| 2012/0229634 A1* | 9/2012 | Laett | G08B 21/043 |
| | | | 348/143 |
| 2012/0316405 A1* | 12/2012 | Taylor | G06F 19/3462 |
| | | | 600/301 |
| 2013/0151274 A1 | 6/2013 | Bage et al. | |
| 2013/0262155 A1 | 10/2013 | Hinkamp | |
| 2014/0085501 A1* | 3/2014 | Tran | H04N 5/23238 |
| | | | 348/222.1 |
| 2014/0094992 A1 | 4/2014 | Lambert et al. | |
| 2014/0155755 A1* | 6/2014 | Pinter | A61B 5/0008 |
| | | | 600/474 |
| 2014/0191861 A1* | 7/2014 | Scherrer | G08B 21/10 |
| | | | 340/501 |
| 2014/0257047 A1 | 9/2014 | Sillay et al. | |
| 2014/0267625 A1* | 9/2014 | Clark | A61B 5/002 |
| | | | 348/46 |
| 2014/0333744 A1* | 11/2014 | Baym | G08B 21/245 |
| | | | 348/77 |
| 2015/0095054 A1* | 4/2015 | Kaigler | G06F 19/3418 |
| | | | 705/2 |
| 2015/0213211 A1 | 7/2015 | Zaleski | |
| 2015/0381947 A1* | 12/2015 | Renkis | H04N 7/181 |
| | | | 348/159 |
| 2016/0022218 A1* | 1/2016 | Hayes | A61G 7/005 |
| | | | 600/301 |
| 2016/0070581 A1* | 3/2016 | Soon-Shiong | G06F 9/453 |
| | | | 715/706 |
| 2016/0110523 A1* | 4/2016 | Francois | G06Q 50/24 |
| | | | 705/2 |
| 2016/0180668 A1* | 6/2016 | Kusens | G16H 40/20 |
| | | | 348/152 |
| 2016/0360034 A1* | 12/2016 | Engelke | H04M 3/42391 |

FOREIGN PATENT DOCUMENTS

| | | | |
|---|---|---|---|
| WO | 9802837 A1 | 1/1998 | |
| WO | 9904043 A1 | 1/1999 | |
| WO | 0062177 A2 | 10/2000 | |
| WO | 0144953 A1 | 6/2001 | |
| WO | 0145014 A1 | 6/2001 | |
| WO | 0233654 A1 | 4/2002 | |
| WO | 2005091203 A2 | 9/2005 | |

OTHER PUBLICATIONS

Foroughi et al, Intelligent video surveillance for monitoring fall detection of elderly in home environment (Year: 2008).*

Litz et al, Covering assisted living key areas based on home automation sensors (Year: 2007).*

E.R. Frykberg, et al., "Terrorist Bombings: Lessons Learned from Belfast to Beirut", Annals of Surgery, vol. 208, No. 5, 1988, pp. 569-576.

AASM, "The International Classification of Sleep Disorders, Revised." Westchester, Illinois; American Academy of Sleep Medicine, pp. 52-58, 2001, http://www.esst.org/adds/ICDS.pdf.

Tipping M.E., "Sparse Bayesian Learning and the Relevance Vector Machine", Journal of Machine Learning Research 1, pp. 211-244, 2001.

Futschik et al., "Prediction of clinical behaviour and treatment for cancers", OMJ Applied Bioinformatics, vol. 2(3), S53-58, 2003, pp. 1-15.

Lorincz, et al., "Sensor networks for emergency response: challenges and opportunities", Pervasive Computing, IEEE, vol. 3, No. 4, pp. 16-23, Oct.-Dec. 2004.

Shawe-Taylor, et al., "Kernel Methods for Pattern Analysis", Cambridge University Press, New York, NY 2004.

Selvin, "Lecture 5", www.biostat.jhsph.edu/.about.beglesto/, 2005.

Singh et al, Authenticated Key Establishment Protocols for a Home Health Care System, 2007.

W. Lutz, W. Sanderson, S. Scherbov, "The coming acceleration of global population ageing", Nature, vol. 451, No. 7179, pp. 716-719, 2008.

Skubic et al, Automated health alerts using in-home sensor data for embedded health assessment, Oct. 29, 2014.

Husebo, Anne Marie et al., "Virtual Visits in Home Health Care for Older Adults", Nov. 20, 2014, Hindawi Publishing Corporation, The Scientific World Journal, vol. 2014, Article ID 689873, 11 pages. https://www.ncbi.nlm.nih.gov/pmc/articles/PMC4258330/.

(56) References Cited

OTHER PUBLICATIONS

Unwin, Brian K. et al., "The Home Visit", Am Fam Physician, Oct. 1, 1999;60(5):1481-1488. https://www.aafp.org/afp/1999/1001/p1481.html.

* cited by examiner

VIRTUAL HOME SAFETY ASSESSMENT FRAMEWORK

CROSS-REFERENCE TO RELATED APPLICATIONS

This application is a continuation of co-pending U.S. patent application Ser. No. 14/564,135 filed Dec. 9, 2014, and titled "Virtual Home Safety Assessment Framework," the entire contents of which are incorporated herein by reference in their entirety.

TECHNICAL FIELD

The present disclosure generally relates to systems and methods for assessing safety.

BACKGROUND

As many as 30% of elderly Americans fall at least once each year. Over half of those falls occur at home, often due to remediable hazards. Hazard remediation typically begins with an expert hazard assessment, but arranging such assessments is beyond the capability of most care-delivery organizations. In addition, the cost of in-person assessments is often beyond the financial means of most patients. A second problem is that most elderly Americans (and their children) would not know how to find an installation contractor to remediate hazards reliably or cost-effectively. The result is that most elderly Americans are consigned to living in homes that are much less safe than they could be.

Paper or computerized forms may be used to increase the efficiency and quality of safety assessments. The forms organize the assessment and management of information on how to mitigate or eliminate certain environmental hazards. Some large care-delivery organizations provide in-person, expert hazard assessments and remediation services to patients. However, such methods are typically costly, inefficient and unaffordable for many patients.

SUMMARY

The present disclosure relates to a framework for facilitating virtual safety assessment. In accordance with one aspect, the framework receives image data of an environment to be assessed for safety from an agent support system. The framework sends such image data to an expert support system and receives safety assessment information from the expert support system determined based on the image data. The framework then provides a report based at least in part on such safety assessment information.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

It is to be understood that the present invention may be implemented in various forms of hardware, software, firmware, special purpose processors, or a combination thereof. Preferably, the present invention is implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or combination thereof) which is executed via the operating system. In addition, various other peripheral devices may be connected to the computer platform such as an additional data storage device and a printing device. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present invention.

It is to be further understood that since at least a portion of the constituent system modules and method steps depicted in the accompanying Figures may be implemented in software, the actual connections between the system components (or the flow of the process steps) may differ depending upon the manner in which the present invention is programmed. Given the teachings herein, one of ordinary skill in the related art will be able to contemplate these and similar implementations or configurations of the present invention.

The present disclosure generally describes a framework (e.g., system) that facilitates virtual safety assessment. In some implementations, the framework receives images of an environment (e.g., care recipient's home) from an agent support system and sends the images to a remotely located expert support system. The expert support system enables, for example, a safety expert to inspect the images, annotate potential safety or fall hazards directly on the images and/or provide safety assessment information (e.g., recommendations for hazard remediation). The framework may then provide a report based at least in part on the safety assessment information to the agent support system and/or to other system. The present framework advantageously facilitates division of labor to make accessible virtual assessment and remediation of safety hazards to a larger number of users at a lower cost. These and other exemplary features and advantages will be described in more detail in the following description.

Figure 1:
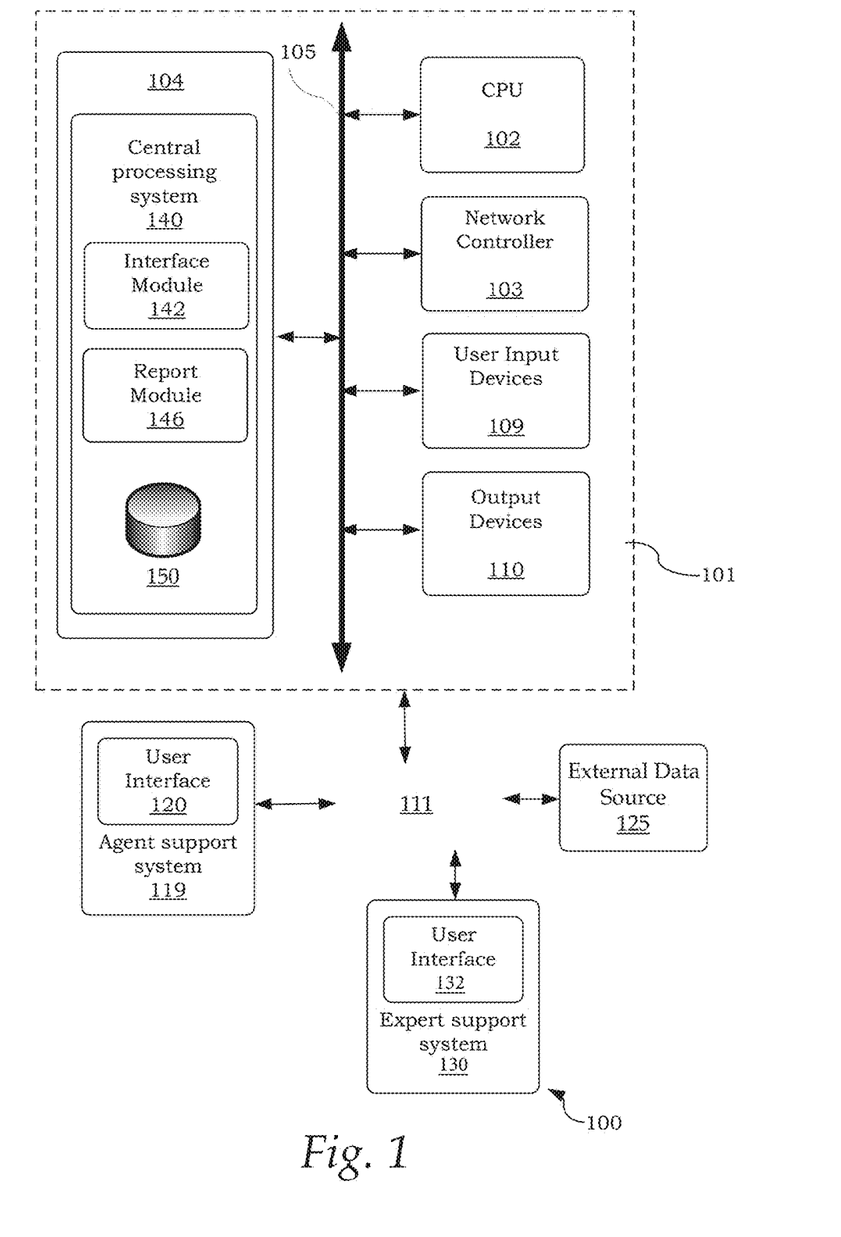
FIG. 1 shows an exemplary architecture.

FIG. 1 shows an exemplary architecture 100 for implementing a method and system of the present disclosure. The computer system 101 may include, inter alia, a processor device such as a central processing unit (CPU) or processor device 102, a non-transitory computer-readable media (or memory device) 104, a network controller 103, an internal bus 105, one or more user input devices 109 (e.g., keyboard, mouse, touch screen, etc.) and one or more output devices 110 (e.g., printer, monitor, external storage device, etc.). Computer system 101 may further include support circuits such as a cache, a power supply, clock circuits and a communications bus. Computer system 101 may take the form of hardware, software, or may combine aspects of hardware and software. Although computer system 101 is represented by a single computing device in FIG. 1 for purposes of illustration, the operation of computer system 101 may be distributed among a plurality of computing devices. For example, it should be appreciated that various subsystems (or portions of subsystems) of computer system 101 may operate on different computing devices. In some such implementations, the various subsystems of the system 101 may communicate over network 111.

The network 111 may be any type of communication scheme that allows devices to exchange data. For example, the network 111 may include fiber optic, wired, and/or wireless communication capability in any of a plurality of protocols, such as TCP/IP, Ethernet, WAP, IEEE 802.11, or any other protocols. Implementations are contemplated in which the system 100 may be accessible through a shared public infrastructure (e.g., Internet), an extranet, an intranet, a virtual private network ("VPN"), a local area network (LAN), a wide area network (WAN), P2P, a wireless communications network, telephone network, facsimile network, cloud network or any combination thereof.

Computer system 101 may communicate with various external components via the network 111. In some implementations, computer system 101 is communicatively coupled to one or more agent support systems 119 and one or more expert support systems 140 that use the services provided by the computer system 101. Agent support system 119 and expert support system 140 may include components (e.g., processor device, non-transitory computer readable media, input devices, output devices, etc.) similar to the computer system 101, and may be in the form of, for example, a desktop computer, laptop, mobile device, smartphone, tablet computer, communication device, browser-based device, wearable computing device, etc. In addition, agent support system 119 and expert support system 130 may each include a user interface (120, 132) (e.g., graphical user interface) for communication of data or information via network 111.

Agent support system 119 is operable by a person who is, or represents, the occupant of the environment to be assessed, such as a caregiver, health worker or even the occupant himself or herself. In some implementations, agent support system 119 may further include an imaging device (e.g., camera) (not shown) that enables the user to capture or acquire image data (e.g., still images, video data, etc.) of the environment, such as the interior or exterior of a care recipient's home. Alternatively, the imaging device is located external to the agent support system 119 and the image data is uploaded from the imaging device to the agent support system 119.

Expert support system 130 is operable by a person who is, or represents, a safety expert, such as a qualified home safety expert. In some implementations, expert support system 130 includes an imaging device, microphone, keyboard or any other input device to facilitate communication with the agent support system 119 in real time.

In some implementations, computer system 101 is communicatively coupled to one or more external data sources 125. External data source 125 may include, for example, a repository of patient records. The patient records may also be locally stored on database 150. Patient records may be computer-based patient records (CPRs), electronic medical records (EMRs), electronic health records (EHRs), personal health records (PHRs), and the like. External data source 125 may be implemented on one or more additional computer systems or storage devices. For example, external data source 125 may include a health information technology (IT) system residing on a separate computer system, a picture archiving and communication system (PACS), or any other now known or later developed hospital, medical institution, medical office, testing facility, pharmacy or other medical patient record storage system.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein may be implemented as computer-readable program code tangibly embodied in non-transitory computer-readable media 104. Non-transitory computer-readable media 104 may include one or more memory storage devices such as random access memory (RAM), read only memory (ROM), magnetic floppy disk, flash memory, other types of memories, or a combination thereof.

The present techniques may be implemented by central processing system 140 stored in computer-readable media 104. In some implementations, central processing system 140 serves to facilitate virtual assessment of safety. Central processing system 140 may include interface module 142, report module 146 and database 150. These exemplary components may operate to assimilate data, transform the data into safety assessment reports, and/or communicate information between the agent support system 119 and the expert support system 130 via, for instance, network 111. It should be understood that less or additional components may be included in the central processing system 140, and the central processing system 140 is not necessarily implemented in a single computer system. The computer system 101 may be a general purpose computer system that becomes a specific purpose computer system when executing the computer-readable program code.

It is to be understood that, because some of the constituent system components and method steps depicted in the accompanying figures can be implemented in software, the actual connections between the systems components (or the process steps) may differ depending upon the manner in which the present framework is programmed. For example, the system 100 may be implemented in a client-server, peer-to-peer (P2P) or master/slave configuration. Given the teachings of the present disclosure provided herein, one of ordinary skill in the related art will be able to contemplate these and similar implementations or configurations of the present framework.

Figure 2:
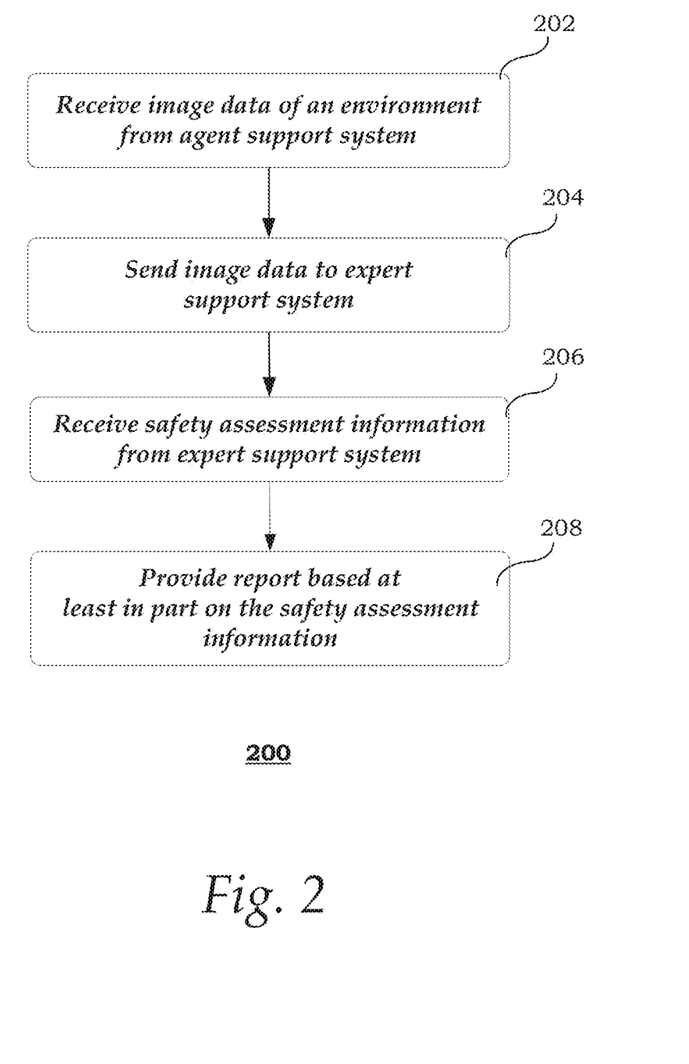
FIG. 2 shows an exemplary method of providing virtual safety assessment.

FIG. 2 shows an exemplary method 200 of providing virtual safety assessment. The steps of the method 200 may be performed in the order shown or a different order. Additional, different, or fewer steps may be provided. Further, the method 200 may be implemented with the system 100 of FIG. 1, a different system, or a combination thereof.

At 202, interface module 142 receives image data of an environment from the agent support system 119. The environment is to be assessed for the safety of an occupant. The occupant may be a person who requires special care or assistance, such as a senior person, baby or a child. The occupant may also be a person with a temporary or permanent disability or illness, such as a blind person, a patient recovering from a body injury (e.g., broken leg) or a newly discharged patient with limited mobility. Alternatively, the occupant may be any other person requesting or requiring safety assessment of his or her environment, such as an employee or worker. The environment may include, for example, the interior and/or exterior of a home, office, place of employment, school, daycare, senior care facility, or any other property that the occupant temporarily or permanently occupies or resides in.

The image data may include still or moving images (e.g., video) of the environment. The image data is acquired by an imaging device (e.g., camera) operated by a user (e.g., health worker or care provider). The imaging device may be included in the agent support system 119 or another external system. As such, the image data may be directly acquired by the agent support system 119, uploaded by another system or downloaded by the agent support system 119.

The user interface 120 in the agent support system 119 may provide directions for operating the imaging device to acquire the image data, such as what environmental elements to capture in the image data, resolution, size of the images, etc. Such directions may be automatically generated by, for example, interface module 142. In some implementations, the user interface 120 enables a user to solicit recommendations on how to address specific safety hazards themselves, price information or competitive bids for hazard mitigation services, or a combination thereof. The user interface 120 may also provide a functionality to enable the user to upload the image data to the computer system 101. Alternatively, the user interface 120 may automatically upload the image data to the computer system 101. The image data may be stored in, for example, database 150.

In some implementations, the user interface 120 is used to establish a two-way communication channel between the agent support system 119 and the expert support system 130 via network 111. Text, sound, image and/or video data may be sent over the communication channel. For example, a live video feed may be provided from the imaging device to the user interface 132 at the expert support system 130. This enables a user at the expert support system 130 to view the image data acquired by the imaging device in real time, and to direct the user in acquiring the image data so as to better capture the relevant environmental elements (e.g., potential safety hazards). Alternatively, the interface module 142 or agent support system 119 may automatically generate and provide such directions based on the live video feed. The directions may include, but are not limited to, instructions in manipulating the imaging device (e.g., placement, field of view, zoom factor, focus, etc.), adjusting the lighting conditions of the environment, etc.

At 204, interface module 142 sends the image data to an expert support system 130. The expert support system 130 may be remotely located away from the agent support system 119. A user at the expert support system 130 may inspect the image data, via the user interface 132, for any potential safety hazard. The user may be, for example, a qualified expert in home safety assessment. Potential safety hazards may include any environmental element that can cause an injury, fall or accident to the occupant, such as a slippery floor, stairs without handrail, uneven steps, dark areas, torn carpet, objects on the floor, and so forth.

In some implementations, the user interface 132 enables the user to manipulate the image data to better visualize the potential safety hazards. Such image manipulation includes, but is not limited to, translation, rotation and/or zooming of the images, changing colors, brightness and/or contrast of the images, creating synthetic camera positions that are different from the actual cameral positions, measuring the length, height, depth and/or distance associated with the elements in the image data, altering lighting levels to simulate night or day, performing light-ray tracing to "look around" corners, etc. The user interface 132 may further enable the user to generate one or more images that visually simulate the environment after hazard remediation is completed. Alternatively, report module 146 or agent support system 119 may automatically generate, based on the image data, the visual simulations of the environment after hazard remediation is completed. If the inspection of the image data is inconclusive (e.g., due to poor quality of image data or poor lighting), the user may personally visit the patient's home to perform a physical inspection for potential safety hazards.

At 206, interface module 142 receives a safety assessment information from the expert support system 130. The safety assessment information may include annotated image data and/or the hazard remediation recommendations. Annotated image data may include graphical indicators (e.g., boundary, arrow, box, circle, etc.) at or around potential safety hazards identified in the image data. Such annotated image data may be generated in response to the user annotating, via user interface 132, directly on the image data to indicate potential safety hazards. For example, the user may use an input device (e.g., mouse, touchpad or touchscreen) to highlight the environment elements that may cause an injury or accident. Alternatively, the annotated image data may be automatically generated by report module 146 in computer system 101 or agent support system 119. Such automatic generation may be performed by invoking, for example, an image recognition algorithm, machine learning algorithm, etc. If the results of the detection algorithms are inconclusive, the computer system 101 or agent support system 119 may initiate an actual person review. For example, the computer system 101 may send a message to the expert support system 130 to request a qualified person to review the image data for potential safety hazards.

User interface 132 may also enable the user to input hazard remediation based on the identified safety hazards and other available patient information. For example, the user may recommend removing or avoiding the safety hazards, improving lighting, installing handrails or grab bars, moving items to make them easier to access, rearranging furniture to provide more room to walk freely, etc. The user may also provide recommendations for patient education, medical supplies, medical services, etc. Alternatively, such recommendations may be automatically generated by report module 146 in computer system 101 or agent support system 119. Such automatic generation may be performed by invoking, for example, a rule-based algorithm.

In some implementations, the user interface 132 presents information about the occupant of the environment that the user may take into account when assessing safety. Such information may include, for example, the patient's age, gender, physical mobility conditions (e.g., wheelchair assisted), specific risk factors from medical history, etc. The patient information may be retrieved from, for example, external data source 125 (e.g., health IT system). Alternatively, the computer system 101 or agent support system 119 may retrieve such information from the external data source 125 and use such information to automatically generate the hazard remediation recommendations.

At 208, report module 146 provides a report based at least in part on the safety assessment. In some implementations, the report module 146 generates the report by including the safety assessment information received from the expert support system 130, such as the annotated image data, hazard remediation recommendations, as well as any other recommendations. It should be appreciated that any of these components of the health assessment information may also be automatically generated by the report module 146, the expert support system 130, the agent support system 119 or any other computer system. If the user of the agent support system 119 is also a customer or client of the service or if the user solicits such information, the report module 146 may include in the report the contact information, pricing and/or competitive bids of one or more installation contractors for addressing identified safety hazards. The one or more installation contractors may be vetted or reviewed by a care-delivery organization for reliability and cost-effectiveness. In addition, report module 146 may support, or include in the report, scheduling, billing and/or payment processing information for the use of the services provided by computer system 101 and/or any other provider In some implementations, the interface module 142 provides the report to the agent support system 119 and/or any other system that requests it and is authorized to receive it. For example, the interface module 142 may provide the report to relevant health information technology (IT) systems for providing, for example, recommended or safety-related medical supplies and/or services. The report may be provided via electronic mail, instant messaging, pop-up notification, made available for on-demand download via a webpage or a dynamic link, or any other communication methods.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A system for providing virtual safety assessments of real-world spaces, the system comprising:
   at least one imaging device in communication with an agent support system;
   at least one processor; and
   at least one non-transitory computer storage media storing computer-useable instructions that,
   when executed by the at least one processor, causes the processor to:
   generate, by the at least one imaging device of the agent support system, image data corresponding to a user environment;
   receive, by an assessment framework via the agent support system, the image data, the image data containing hazard information associated with the user environment, wherein the hazard information includes one or more environmental elements that present a risk to a user of the user environment;
   provide, by the assessment framework, the image data to an expert support system, the expert support system configured to process the image data by inspecting environmental elements associated with the image data;
   receive, by the assessment framework, processed image data via the expert support system, the processed image data comprising safety assessment information, wherein the safety assessment information comprises at least one of annotated image data and hazard remediation recommendations; and
   generate, by a report module of the assessment framework, a report based at least on the processed image data, the report comprising the safety assessment information.

2. The system of claim 1, further comprising causing the processor to provide the report to the agent support system.

3. The system of claim 1, wherein the agent support system is at least one of a mobile device and a wearable user device.

4. The system of claim 1, wherein the image data comprises at least one of video image data and still image data.

5. The system of claim 1, further comprising causing the processor to:
   generate, by the assessment framework, operational directions for acquiring the image data; and
   provide, to the agent support system, the operational directions.

6. The system of claim 1, wherein the assessment framework facilitates the establishment of a real-time communication channel between the agent support system and the expert support system.

7. The system of claim 1, wherein the expert support system comprises at least one expert interface that enables the manipulation of the image data to enhance visualization of the user environment.

8. The system of claim 1, wherein the expert support system generates, based on the processed image data, one or more visual simulations of the user environment after a hazard remediation is completed.

9. The system of claim 1, further comprising causing the processor to:
   receive, by the expert support system, information associated with the user of the user environment; and
   determine the assessment information based at least in part on the image data and the user information.

10. A computer-implemented method for facilitating and providing a virtual safety assessment, the method comprising:
    acquiring, via an imaging device, image data corresponding to a user environment;
    receiving, by a central processing system, the image data;

providing, by the central processing system, the image data to an expert support system, the expert support system configured to transform the image data into processed image data;

receiving, by the central processing system via the expert support system, the processed image data, the processed image data comprising assessment information, the assessment information based on the image data;

generating, by a report module, a report based at least on the processed image data, the report comprising at least one of annotated image data and hazard remediation recommendations; and providing, by the central processing system, the report to a user of the user environment.

11. The method of claim 10, wherein the imaging device is in communication with at least one of a mobile device and a wearable user device.

12. The method of claim 10, wherein the image data is at least one of video image data and still image data.

13. The method of claim 11, wherein the report is provided for display on the at least one of the mobile device and the wearable user device.

14. The method of claim 10, wherein the expert support system enables the manipulation of the image data to enhance virtual safety hazard visualization.

15. At least one non-transitory computer storage media, having instructions thereon that, when executed by at least one processor of a computing system, cause the computer system to:

obtain, by an imaging device in communication with an agent support device, image data corresponding to at least one user environment;

provide, by an assessment system, the image data to an expert support system;

receive, by the assessment system, processed image data comprising safety assessment data, the safety assessment data based on the image data; and automatically generate, by a report module of the assessment system, a report based on at least the safety assessment information, the report comprising at least one of annotated image data and hazard remediation recommendations.

16. The computer storage media of claim 15, wherein the agent support device is a mobile device; and wherein the instructions further cause the computing system to:

provide the report to the mobile device, wherein the mobile device renders the report for display.

17. The computer storage media of claim 15, wherein the agent support device is configured to solicit at least one of specific remediation sequences and competitive bids for hazard mitigation services based on the image data.

18. The computer storage media of claim 15, wherein the instructions further cause the computing system to:

receive environment occupant information; and generate the safety assessment data based on at least the image data and the occupant information.

* * * * *

UNITED STATES PATENT AND TRADEMARK OFFICE
CERTIFICATE OF CORRECTION

PATENT NO.         : 10,198,780 B2
APPLICATION NO.    : 15/661989
DATED              : February 5, 2019
INVENTOR(S)        : James M. Walker et al.

It is certified that error appears in the above-identified patent and that said Letters Patent is hereby corrected as shown below:

In the Specification

Column 07, Line 41: Please remove "provider" and replace with --provider.--.

Signed and Sealed this
Ninth Day of April, 2019

Andrei Iancu
*Director of the United States Patent and Trademark Office*